United States Patent
Plompen et al.

(10) Patent No.: US 8,502,133 B2
(45) Date of Patent: Aug. 6, 2013

(54) WATER PHANTOM

(75) Inventors: Rob Plompen, Nürnberg (DE); Lutz Müller, Nürnberg (DE)

(73) Assignee: Ion Beam Applications S.A., Louvain-la-Neuve ( * ) Notice: Subject to any disclaimer, the term of this patent is extended or adjusted under 35 U.S.C. 154(b) by 639 days.

(21) Appl. No.: 12/299,452

(22) PCT Filed: May 7, 2007

(86) PCT No.: PCT/BE2007/000044
§ 371 (c)(1),
(2), (4) Date: Jun. 11, 2010

(87) PCT Pub. No.: WO2007/128087
PCT Pub. Date: Nov. 15, 2007

(65) Prior Publication Data
US 2010/0243875 A1    Sep. 30, 2010

(30) Foreign Application Priority Data
May 5, 2006 (EP) .................................. 06113586

(51) Int. Cl.
*G01D 18/00* (2006.01)
(52) U.S. Cl.
USPC .................................................... 250/252.1
(58) Field of Classification Search
USPC .................................................. 250/252.1
See application file for complete search history.

(56) References Cited

U.S. PATENT DOCUMENTS

| | | | |
|---|---|---|---|
| 5,006,714 A | | 4/1991 | Attix |
| 5,143,745 A | * | 9/1992 | Maganas et al. ............... 427/8 |
| 5,621,714 A | | 4/1997 | Kobayashi et al. |
| 5,627,367 A | * | 5/1997 | Sofield ........................ 250/252.1 |
| 6,009,572 A | * | 1/2000 | Morris ........................... 4/496 |
| 6,207,952 B1 | | 3/2001 | Kan et al. |
| 2004/0228435 A1 | | 11/2004 | Russell |

FOREIGN PATENT DOCUMENTS

| | | |
|---|---|---|
| DE | 19606809 C1 | 3/1997 |
| FR | 2723212 A1 | 2/1996 |
| JP | 2182271 A | 7/1990 |
| JP | 2001346894 A | 12/2001 |
| JP | 2003047666 A * | 2/2003 |

OTHER PUBLICATIONS

Bonin et al., "A pixel chamber to monitor the beam performance in hadron therapy," 2004, Nuclear Instruments and Methods in Physics Research A, vol. 519, pp. 674-686.*

* cited by examiner

*Primary Examiner* — Kiho Kim
(74) *Attorney, Agent, or Firm* — Fitch, Even, Tabin & Flannery LLP

(57) ABSTRACT

The present invention is related to a water phantom for measuring and determining the dose distribution of radiation produced by a particle beam or photon radiation beam comprising: a water tank; means for varying the water level in said water tank; an acquisition detector positioned in a fixed position related to the water tank opposite to the beam, wherein said acquisition detector is a two dimensional detector comprising a plurality of sensors and capable of simultaneously measuring the dose in a plurality of points in an area. Subsequent measurements are performed varying each time the water level within the water tank, until the dose distribution in the entire volume of the water tank is obtained.

20 Claims, 4 Drawing Sheets

WATER PHANTOM

CROSS-REFERENCE TO RELATED APPLICATIONS

This application is a U.S. national phase application filed under 35 U.S.C. §371 of International Application PCT/BE2007/000044, filed on May 7, 2007, designating the United States, which claims priority from EP 06113586.9, filed May 5, 2006, which are hereby incorporated herein by reference in their entirety.

FIELD OF THE INVENTION

The present invention is related to a water phantom for measuring and checking the dose distribution of a particle beam or photon radiation beam produced by a radiation therapy apparatus.

STATE OF THE ART

Water phantoms are used in radiation therapy for acceptance testing, commissioning and quality assurance (QA) measurements. Acceptance tests are detailed test procedures, performed normally once in the lifetime of a radiation therapy apparatus, in the factory, in order to assure the validity of the specifications of the radiation therapy apparatus, and to verify that the final deliverable meets the client's requirements and agreements. Commissioning tests of radiation therapy treatment planning systems (TPS) comprise a series of tasks which require an extensive set of measurements of radiation dose profiles. By using these data specific to a radiation therapy apparatus, the TPS can be tuned to deliver the required dose and dose distribution. Commissioning tests must be performed each time a TPS is installed or modified. The length of time needed depends on many factors, such as availability and experience of personnel and proper instrumentation and type of accelerator. A single energy photon machine can be commissioned in about 2 to 4 weeks. A multimodality accelerator with two photon energies and several electron energies can take about 6 to 8 weeks of intensive effort (requiring 16 hours shifts). QA test are performed at regular intervals for assuring that beams delivered by the radiation therapy apparatus remain within the specifications.

A water phantom known in the art uses a single point radiation dose detector such as an ionization chamber or a diode and comprises means for moving said detector at successive locations in the radiation field. Such systems typically comprise a water tank (having a volume of about 200 liters), equipped with a mechanism for moving a radiation sensor such as a water-tight air ion chamber probe or a diode in the water volume. One example of such a water phantom is the "Blue Phantom" manufactured by the applicant. In such a water phantom, the detector is positioned in a location where a measurement is desired, the radiation beam is emitted while the measurement is taken, and then stopped. The detector is then moved to a next position until a full dose map is obtained. This procedure is time consuming, and moreover, depends on the stability of the beam characteristics among measurements. In addition, this process cannot be applied to radiation delivery methods where collimators are moved while irradiating, such as the virtual wedge method or IMRT.

Another water phantom known in the art uses a linear array of detectors. Such a linear array is moved in two dimensions in a water tank, in order to build a three dimensional map of the radiation field. One example of such a linear array of detectors is the LDA-99 comprising 99 diodes with 5 mm spacing manufactured by the applicant and can be used in the "Blue Phantom" of the applicant.

The detectors to be used with such water phantoms obviously must be of a water resistant construction. This can be a problem, especially when using ionisation chambers as sensors.

Measurement of the radiation fields can be made in two different configurations. In TPR (Tissue to Phantom Ratio) or SAD (source acquisition distance, FIG. 1a) configuration, the source-to-detector distance is fixed as the source-to-water phantom surface distance varies. TPR or SAD configuration requires that the water phantom is equipped with a filling level sensor and a bi-directional pumping control allowing adjustment of the water level. In DD (Depth-Dose) or SSD (source to surface distance, FIG. 1b) configuration, the source-to-water phantom surface distance is kept constant as the source-to-detector distance varies.

Though the use of such a phantom is an established standard since many years, the handling of these large scanning water phantoms is cumbersome and time consuming.

A conventional water phantom is described in document U.S. Pat. No. 5,621,214. This document discloses a radiation beam scanner system which employs two ion chamber detectors, signal and reference, positioned within the water tank and out of the water tank, respectively. Means to move the signal detector within the water tank are also disclosed. This document presents some drawbacks as follows: the 3D scanning allows the measurement of one point in space at a time, which requires several days for complete TPS commissioning tests; moreover, due to the large water volume, phantoms are coupled to a moveable water tank and are mounted on a moveable support table. Owing to their weight, they cannot be positioned on the patient couch.

Another water phantom is described in U.S. Pat. No. 5,006,714 which discloses a scintillator dosimetry probe positioned into a phantom for detecting high-energy beam dosimetry. The scintillator creates a light converted to an output signal proportional to the radiation dose-rate incident, the latter being incident upon the scintillator. Mechanical scanning means for moving the detector within the phantom are also disclosed. Once more the 3D scanning allows the measurement of one point in space at a time, requiring several days for complete TPS commissioning tests.

Another water phantom is described in U.S. Pat. No. 6,207,952. The document discloses a water phantom type dose distribution determining apparatus wherein a closed water tank is filled with water, and a sensor is positioned into this tank. The tank is attached to an irradiation nozzle in a rotating gantry. The sensor is moveable within the water tank, and the water tank is moveable with respect to the nozzle attachment. Nevertheless this water phantom presents the same drawbacks of the water phantoms discussed herein above in that a time consuming process of displacements and measurements is needed, and that the measurement of time-dependent radiations fields such as the virtual wedge method or IMRT is not possible.

Another water phantom is disclosed by FR-A-2723212. This water phantom comprises a compact detector device which is moved within the water phantom by mechanical means. Said device comprises a plurality of detectors located along the length thereof. Each detector device is therefore a one-dimension detector and the use thereof requires mechanical movement means for moving said detector device. As a consequence, this water phantom is time consuming and needs several days for complete TPS commissioning tests.

Another water phantom is disclosed by JP2001346894 which relates to a scintillator having a plane vertical to the direction of the radiation beam. The scintillator is moved within the water tank by mechanical means and provides measurements of the absorbed dose. However, such a device has some drawbacks as follows:

the response of the scintillator to radiations is strongly dependent on energy of the radiation beam and therefore is not sufficient for quality requirements;

Cerenkov radiations emitted from water traversed by radiations would strongly interfere with measurements;

the use of mechanical means, which are required for moving the scintillator within the water tank, make the measurements process time consuming;

it is not possible to perform source to surface distance measurements (SAD measurements).

However, all above-discussed water phantoms cannot provide measurements of time-dependent fields, since scanning detectors measure said radiation fields at different times. Moreover, it is not possible to perform measurements in a shallow depth (for example less than 1 cm).

AIMS OF THE INVENTION

The present invention aims to provide a water phantom for easily measuring the absorbed dose to water that allows to overcome all above-discussed drawbacks of prior art.

SUMMARY OF THE INVENTION

According to a first aspect of the present invention a water phantom for measuring and determining the dose distribution of radiation produced by a particle beam or photon radiation beam is provided. The water phantom comprises a water tank having a base, an acquisition detector and means for varying the water level in said water tank. The acquisition detector is a two-dimensional detector, preferably comprising a plurality of sensors for simultaneously measuring the dose in a plurality of points in an area, said area corresponding essentially to the base of the tank. This allows an easier and faster measure the dose distribution. Said detector is preferably attached or in a fixed relationship with the water tank and is positioned in a position related to the tank opposite to the beam source. Namely, if said beam is a vertical beam irradiating the top of the water tank, the acquisition detector is located in a fixed position related to the tank under and beneath said water tank. Said detector being preferably positioned outside the water tank.

Furthermore, due to the absence of any mechanical positioning device of the detector and/or the sensor, the radiation field arriving at the acquisition detector is not disturbed by these means. Furthermore, the absence of mechanical positioning means obviously reduces costs.

In an advantageous embodiment, said plurality of sensors is a plurality of ionization chambers.

Advantageously the water phantom is further provided with a lateral reservoir and a bi-directional pumping system for pumping water between the water tank and the lateral reservoir.

In a specific embodiment, the water phantom further comprises a water level sensor for controlling the water level in the water tank.

In a typical embodiment, the acquisition detector is coupled to read-out electronics located beneath the lateral reservoir.

In another preferred embodiment, the water phantom comprises means for varying the relative water level in the water tank and the vertical position corresponding to the height of said water tank in equal amplitude but opposite directions in such a way that the absolute water height in the water tank remains constant so that the source-to-water phantom surface distance is maintained constant as the source-to-detector distance is varying.

According to a second aspect of the invention, there is provided a method for measuring and determining the dose distribution of radiation produced by a particle beam or photon radiation beam in a volume using a device comprising a water tank and a two-dimensional acquisition detector and comprising a plurality of sensors. Said detector is preferably attached or in a fixed relationship with the water tank and is positioned in a position related to the tank opposite to the beam source. Namely, if said beam is a vertical beam irradiating the top of the water tank, the acquisition detector is located in a fixed position related to the tank under and beneath said water tank. Said detector being preferably positioned outside the water tank.

This method comprises the steps of: measuring simultaneously the dose distribution in a plurality of points in a defined area essentially corresponding to the base of the tank by using said acquisition detector; varying the water level within the water tank and repeating said measurements until the dose distribution in the entire volume of the water tank is obtained.

A preferred embodiment of the method according to the second aspect of the invention comprises the steps of: adjusting the water level in the water tank to different subsequent values; keeping each time the acquisition detector fixed with respect to said water tank; providing a two-dimensional measure for each value of the water level in the water tank until the dose distribution is obtained in the entire water tank volume.

Another preferred embodiment of the method according to the second aspect of the invention comprises the steps of: performing measurements with the absolute water height in the water tank constant as the relative water level in said water tank and the vertical position corresponding to the height of the lift table are adjusted to subsequent values in such a way that the source-to-water phantom surface distance is maintained constant as the source-to-detector distance is varying; providing a two-dimensional measure for each value of the previous step until the dose distribution is obtained in the entire water tank volume.

Preferably, according to the second aspect of the invention, said plurality of sensors is a plurality of ionization chambers.

According to a third aspect of the invention, there is provided a use of the device or method according to the invention for commissioning tests of a radiation therapy apparatus, thereby drastically reducing the time amount required.

SHORT DESCRIPTION OF THE DRAWINGS

DETAILED DESCRIPTION OF PREFERRED EMBODIMENTS OF THE INVENTION

Figure 1A:
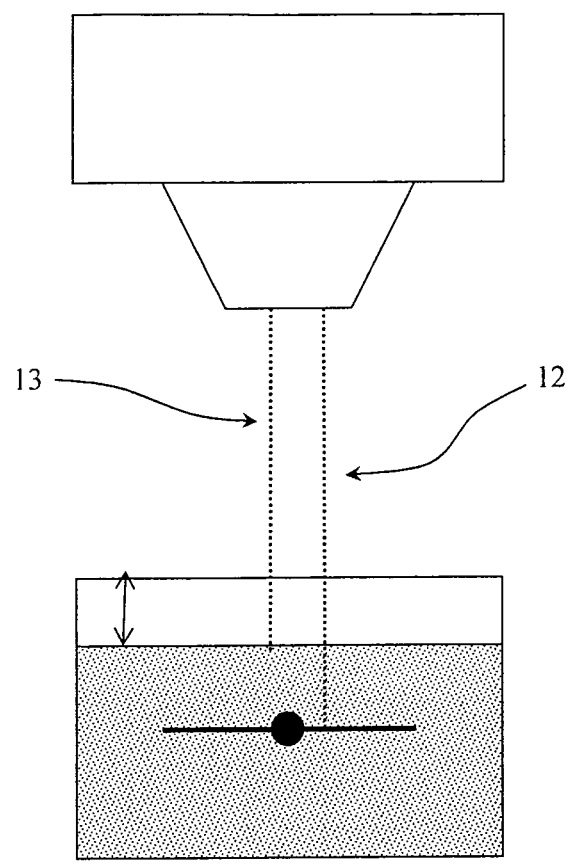
FIG. 1a represents a DD (Depth-Dose) or SSD (source to surface distance) measurement configuration.
Figure 1B:
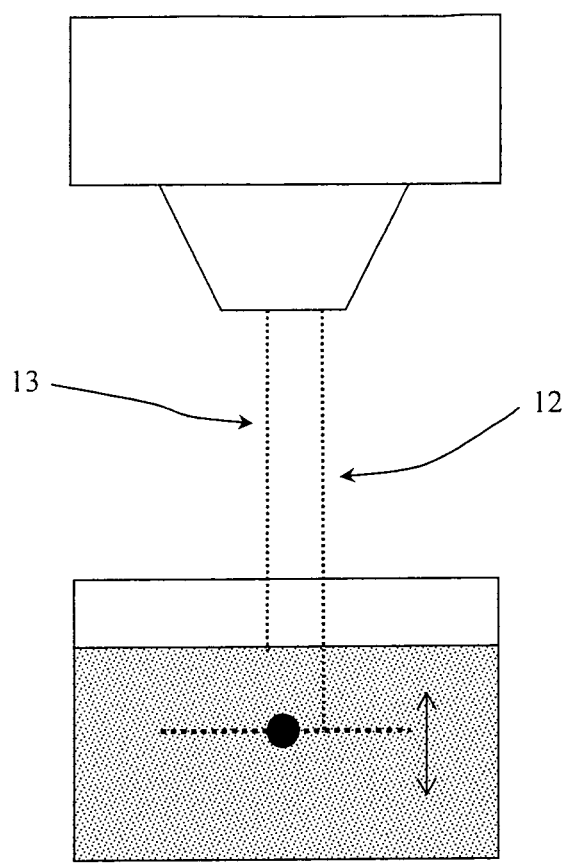
FIG. 1b represents a TPR (Tissue-to-Phantom Ratio) or SAD (source acquisition distance) measurement configuration.

FIGS. 1a and 1b represent the principle of measurement made in two different configurations. In said figures, the tank is positioned essentially on a horizontal plane while the incident beam is irradiating the top of said tank, essentially according to a vertical axis. Namely, FIG. 1a is representing the TPR (Tissue to Phantom Ratio) or SAD (source acquisition distance) configuration, where the source-to-detector distance is fixed as the source-to-water phantom surface distance varies, while FIG. 1b is representing the DD (Depth-Dose) or SSD (source to surface distance) configuration, where the source-to-water phantom surface distance is kept constant as the source-to-detector distance varies.

Figure 2:
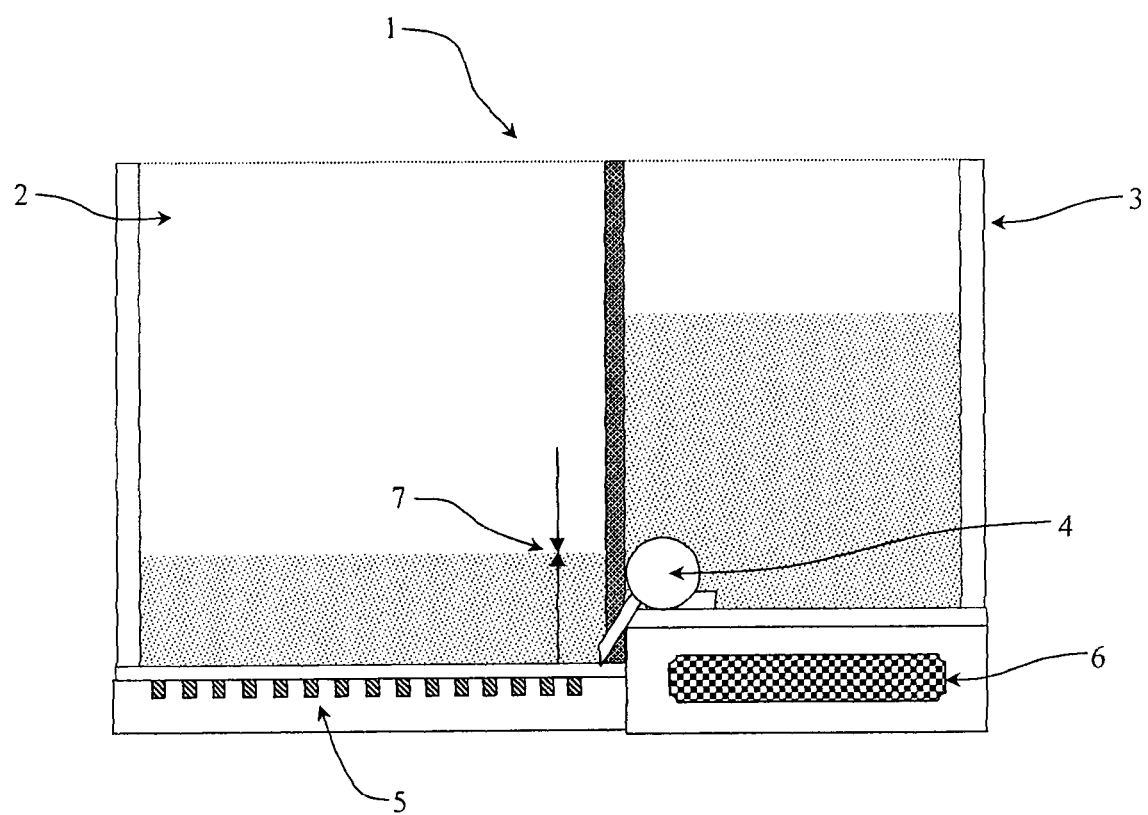
FIG. 2 is a side view illustrating the overall configuration of a water phantom according to one embodiment of the invention.

Embodiments of the invention described hereinafter present the following features:
1. Measurements of the radiation dose can be performed in either SAD or SSD configuration;
2. Instead of taking a set of measurements using a scanning device, a plurality of sensors takes one complete area measurement at a time;
3. The total water volume for an active area of 40×40 cm and a maximum measurement depth of 30 cm is 48 l. Together with the other components of the phantom (ca. 15 kg) the total weight is less than 70 kg. Therefore the water phantom can be placed on the patient couch. Thereby the position of the water phantom can be adjusted in X-, Y-, Z-axis with a precision of ca. 1 mm. Also the angular position can be adjusted with high precision. This feature allows, in one of the preferred embodiments of the invention, to perform measurements in the SSD configuration.
4. Larger phantom according to the invention can also be realized with a separate lift table;

FIG. 2 shows in detail one preferred embodiment of the invention, wherein SAD type measurements may be performed. The water phantom 1 of this embodiment comprises an acquisition detector 5 composed of a matrix of ion chambers situated in one plane. The matrix comprises 1020 individual ionisation chambers, but matrices having less (100) or more (10000) chambers may also be used. A water tank 2 is placed over the acquisition detector matrix 5 and comprises a water level sensor 7. A lateral reservoir 3 is provided with a bi-directional pumping system 4 for adjusting the water level in the water tank 2 in such a way that the source-to-water phantom surface distance may be varied. Under said lateral reservoir 3, the water phantom 1 is provided with read-out circuits 6 with one charge converting channel for each chamber of the acquisition detector matrix 5 for measuring the charges or currents produced by a radiation beam. Read-out values are processed by independent counter circuits for each channel and the counter values can be further integrated to a second set of registers for a synchronous read-out of all channels. A host computer running data analysis software and a micro-controller based system for controlling the acquisition channels and the water levelling are also provided.

In this preferred embodiment of the invention, SAD type dose measurements are performed as follows: once the water phantom 1 has been positioned and filled up to required level by means of the bi-directional pumping system 4 and of the water level sensor 7, measurements in a plurality of points in an area are performed simultaneously with the acquisition detector 5 stationary below said water tank 2. The collected data are processed by the read-out circuits 6 and a two-dimensional dose map is thereby obtained. The water level in the water tank is then adjusted to a different subsequent value. Two-dimensional measurements are then performed with the acquisition detector 5 still located below said water tank 2. The above described measurements are performed until the dose distribution is obtained in the entire volume in the water tank 2.

Figure 3:
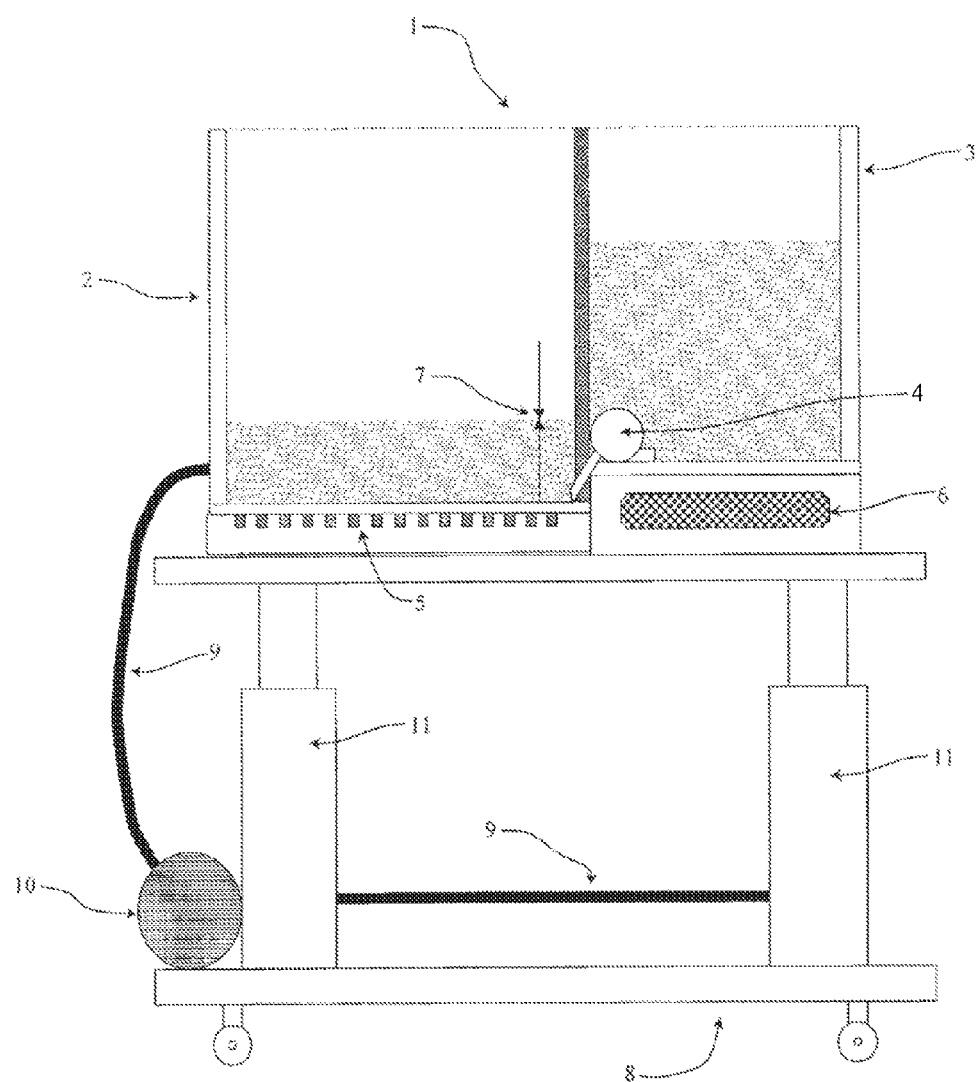
FIG. 3 is a side view illustrating a water phantom according to another embodiment of the invention.

FIG. 3 shows in detail, another preferred embodiment of the invention. As mentioned above, the water phantom 1 can also be used for SSD type measurements if it is combined with a lift mechanism, which could be the patient couch or a lift table 8. A water phantom 1 of this embodiment comprises, in addition with respect to the above discussed embodiment, a pump 10 and a lift table 8 with hydraulic pistons 11. In this embodiment, the relative water level in the water tank 2 and the lift table 8 are moved in equal amplitude but opposite directions in such a way that the absolute water height in the water tank 2 remains constant so that the source-to-water phantom surface distance is maintained constant as the source-to-detector distance is varying. This synchronous movement can be realized using the pump 10 which transfers water from the water tank 2 to the hydraulic pistons 11 by means of a connection line 9. Said lift table 8 can use n hydraulic cylinders whose cross section is $B_n$, respectively. If the water level of the water tank 2 is A, fulfilling of the condition: $\Sigma B_n = A$, assures the required motion of both water column in the water tank 2 and the hydraulic pistons 11 of the lift table 8. The fulfillment of the above condition is nevertheless difficult, as the cross section of the water tank 2 might change with position and depending on the filling level. In order to overcome this difficulty, the lateral reservoir 3 and the bi-directional pumping system 4 serve the purpose of correcting the water level of the water tank 2 in order to fulfil the condition that the absolute water height in the water tank 2 remains constant.

In this preferred embodiment of the invention, SSD type dose measurements are performed as follows: The source-to-surface distance is adjusted by, on the one hand, adjusting the relative level in the tank with pumping system 4, and, on the other hand, the vertical position of the water phantom by means of the lift table 8, the pump 10 and the hydraulic pistons 11. Measurements in a plurality of points in an area are performed with the acquisition detector 5 stationary below said water tank 2. Subsequent two-dimensional measurements are performed with the absolute water height in the water tank 2 constant as the relative water level in the water tank 2 and the lift table 8 are varied as above described. The collected data are each time processed by the read-out circuits 6 until the dose distribution is obtained in the entire volume of the water tank 2.

The water phantom according to the invention presents many advantages:
By using the water phantom of the invention, the QA procedure is much faster and easier (typically from a few hours to half a day using the prior-art phantoms) to less than one hour when using a phantom according to the invention. Therefore, QA tests can be performed more often and in a more complete way.
The water phantom of the invention is much lighter (typically less than 70 kg) than a prior-art water phantom. Therefore, the water phantom can also be positioned on the patient couch, instead of on a special support. Thereby, one can use the precise translation and rotation position controls of the patient couch, and precisely determine the position of the radiation field distribution with respect to the patient couch.
Due to the absence of any mechanical sensor positioning means, the radiation fields arriving at the detector are not disturbed by these means. Moreover, its simplicity obviously reduces costs.
One of the most perturbing drawbacks of the prior art is the enormous time amount usually required for the commissioning tests of a TPS. By using the water phantom of the invention, one can drastically reduce this time amount, overcoming said drawback.

An important feature of the invention relates to the fact that the 2D detector is not immersed and nor moved in water. This fact avoids providing difficult and imprecise mechanical means.

The invention claimed is:

1. A water phantom effective for measuring and determining the dose distribution of radiation produced by a particle beam or photon radiation beam source comprising: a water tank; means which varies the water level in said water tank; an acquisition detector positioned in a fixed position with respect to said water tank and opposite to the beam source with respect to said water tank; wherein said acquisition detector is a two dimensional detector comprising a plurality of sensors and capable of simultaneously measuring the dose in a plurality of points in an area, wherein said acquisition detector is positioned underneath said water tank so as to measure the dose delivered in an area corresponding to the bottom of the tank, when the beam is an essentially vertical beam irradiating the top of the water tank.

2. The water phantom according to claim 1, wherein said plurality of sensors is a plurality of ionization chambers.

3. The water phantom according to claim 2, wherein said means for varying water level are adjusting the water level in the water tank in such a way that the source-to-water phantom surface distance is varying.

4. The water phantom according to claim 3, wherein means for controlling the water level comprise a water level sensor.

5. The water phantom according to claim 1, wherein said means for varying water level comprise a lateral reservoir and a bi-directional pumping system for pumping water between the water tank and the lateral reservoir.

6. The water phantom according to claim 5, wherein the acquisition detector is coupled to read-out electronics located beneath said lateral reservoir.

7. The water phantom according to claim 1, further comprising means for controlling the water level in the water tank.

8. The water phantom according to claim 1, wherein said means which varies the water level in said water tank comprise means for varying the vertical position of said water tank and accordingly said water level with an equal amplitude but in two opposite directions.

9. The water phantom according to claim 8, wherein said means which varies the vertical position of said water tank comprise a lift table with hydraulic pistons connected to a pump that transfers water from said water tank pump to the hydraulic pistons by means of a connection line.

10. The water phantom according to claim 9, wherein the relative water level in the water tank and the lift table are moved in such a way that the absolute water height in the water tank remains constant, so that the source-to-water phantom surface distance is maintained constant as the source-to-detector distance is varying.

11. A method of commissioning a radiation therapy apparatus, the method comprising utilizing the water phantom according to claim 1.

12. A method for measuring and determining the dose distribution of radiation produced by a particle beam or photon radiation beam in a volume using a device comprising a water tank and a two-dimensional acquisition detector located in a fixed position beneath said water tank and comprising a plurality of sensors, wherein the method comprises the steps of:
    directing the beam at the top of the tank, essentially according to a vertical direction;
    measuring simultaneously the dose distribution in a plurality of points in an area corresponding to the bottom of the tank, by using said acquisition detector;
    varying the water level within the water tank and repeating said measuring step until the dose distribution in said volume is obtained.

13. The method according to claim 12, wherein the measurement of the dose distribution is performed by adjusting the water level in the water tank to different subsequent values and keeping the acquisition detector fixed with respect to said water tank.

14. The method according to claim 12, wherein the measurement of the dose distribution is performed by moving the relative water level in the water tank and the lift table in equal amplitude but opposite directions in such a way that the absolute water height in the water tank remains constant, and with the acquisition detector stationary below said water tank, so that the source-to-water phantom surface distance is maintained, during each measurement, constant, as the source-to-detector distance is varying.

15. The method according to claim 12, wherein said plurality of sensors is a plurality of ionization chambers.

16. A water phantom for measuring and determining the dose distribution of radiation produced by a particle beam or photon radiation beam source comprising: a water tank; a control device configured to vary the water level in the water tank; an acquisition detector positioned in a fixed position with respect to the water tank and opposite to the beam source with respect to the water tank; wherein the acquisition detector is a two dimensional detector comprising a plurality of sensors and capable of simultaneously measuring the dose in a plurality of points in an area, wherein the acquisition detector is positioned underneath the water tank and is effective to measure the dose delivered in an area corresponding to the bottom of the tank, when the particle beam or photon radiation beam is an essentially vertical beam irradiating the top of the water tank.

17. The water phantom according to claim 16, wherein the control device comprises a lateral reservoir and a bi-directional pumping system for pumping water between the water tank and the lateral reservoir.

18. The water phantom according to claim 17, wherein the acquisition detector is coupled to read-out electronics located beneath the lateral reservoir.

19. The water phantom according to claim 16, wherein the control device comprises a positioning device configured to vary the vertical position of the water tank and the water level with an equal amplitude but in two opposite directions.

20. The water phantom according to claim 19, wherein the positioning device comprises a lift table with hydraulic pistons connected to a pump that transfers water from the water tank pump to the hydraulic pistons via a connection line.

* * * * *

UNITED STATES PATENT AND TRADEMARK OFFICE
CERTIFICATE OF CORRECTION

PATENT NO. : 8,502,133 B2  
APPLICATION NO. : 12/299452  
DATED : August 6, 2013  
INVENTOR(S) : Plompen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1223 days.

Signed and Sealed this
Fifteenth Day of September, 2015

Michelle K. Lee
*Director of the United States Patent and Trademark Office*